United States Patent
Forsberg et al.

(10) Patent No.: US 11,482,334 B2
(45) Date of Patent: Oct. 25, 2022

(54) CONTEXTUALIZED PATIENT-SPECIFIC PRESENTATION OF PREDICTION SCORE INFORMATION

(71) Applicant: KONINKLIJKE PHILIPS N.V., Eindhoven (NL)

(72) Inventors: Thomas Andre Forsberg, Hayward, CA (US); Merlijn Sevenster, Haarlem (NL); Yugang Jia, Winchester, MA (US); Ayman Alalao, Cambridge, MA (US); Qianxi Li, Cambridge, MA (US); Yuechen Qian, Lexington, MA (US); John Blair, Chicago, IL (US); Eran Rubens, Palo Alto, CA (US); Brian David Gross, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 180 days.

(21) Appl. No.: 16/632,631

(22) PCT Filed: Jul. 20, 2018

(86) PCT No.: PCT/EP2018/069698
§ 371 (c)(1),
(2) Date: Jan. 21, 2020

(87) PCT Pub. No.: WO2019/020497
PCT Pub. Date: Jan. 31, 2019

(65) Prior Publication Data
US 2020/0168338 A1 May 28, 2020

Related U.S. Application Data (60) Provisional application No. 62/536,582, filed on Jul. 25, 2017.

(51) Int. Cl.
*G16H 50/30* (2018.01)
*G16H 15/00* (2018.01)
(Continued)

(52) U.S. Cl.
CPC ............ *G16H 50/30* (2018.01); *A61B 6/481* (2013.01); *G06F 16/26* (2019.01); *G06N 5/04* (2013.01);
(Continued)

(58) Field of Classification Search
None
See application file for complete search history.

(56) References Cited

U.S. PATENT DOCUMENTS 8,060,185 B2 11/2011 Hunter
10,213,145 B1 * 2/2019 McNair .............. A61B 5/02416
(Continued)

FOREIGN PATENT DOCUMENTS

| EP | 0975272 | 2/2000 |
| WO | 2013/142268 A1 | 9/2013 |
| WO | 2016/079654 | 5/2016 |

OTHER PUBLICATIONS

International Search Report and Written Opinion dated Sep. 21, 2018 for International Application No. PCT/EP2018/069698 filed Jul. 20, 2018.

*Primary Examiner* — John A Pauls (57) ABSTRACT

A patient monitor (8) includes a display (10). Patient values (38) are obtained for one or more known variables of a risk prediction function (30). One or more unknown variables of the risk prediction function are determined, and at least one hyperplane (40) is defined as values assumable by the one or more unknown variables. Values of the risk prediction function are computed over the at least one hyperplane using the obtained patient values. A visualization template is selected from a database of visualization templates (50) using template selection indices including the risk prediction function and the one or more unknown variables. Using the visualization template, a visualization (52) of the computed values of the risk prediction function over the at least one hyperplane is displayed.

21 Claims, 3 Drawing Sheets

(51) Int. Cl.
　　　*G16H 50/20*　　　(2018.01)
　　　*G16H 30/40*　　　(2018.01)
　　　*G16H 40/63*　　　(2018.01)
　　　*G06F 16/26*　　　(2019.01)
　　　*A61B 6/00*　　　(2006.01)
　　　*G06N 5/04*　　　(2006.01)

(52) U.S. Cl.
　　　CPC ............. *G16H 15/00* (2018.01); *G16H 30/40* (2018.01); *G16H 40/63* (2018.01); *G16H 50/20* (2018.01)

(56) References Cited

U.S. PATENT DOCUMENTS

| | | | |
|---|---|---|---|
| 11,257,574 B1* | 2/2022 | Boussios | G06N 20/00 |
| 2012/0060216 A1* | 3/2012 | Chaudhri | G16H 70/00 |
| | | | 726/21 |
| 2013/0231949 A1 | 9/2013 | Baronov | |
| 2017/0154162 A1 | 6/2017 | Balasubramanian | |

* cited by examiner

CONTEXTUALIZED PATIENT-SPECIFIC PRESENTATION OF PREDICTION SCORE INFORMATION

CROSS REFERENCE TO RELATED APPLICATIONS

This application is the U.S. National Phase application under 35 U.S.C. § 371 of International Application No. PCT/EP2018/069698 filed Jul. 20, 2018, published as WO 2019/020497 on Jan. 31, 2019, which claims the benefit of U.S. Provisional Patent Application No. 62/536,582 filed Jul. 25, 2017. These applications are hereby incorporated by reference herein.

FIELD

The following relates generally to the patient monitoring arts, electronic patient monitor arts, electronic clinical decision support arts, and related arts.

BACKGROUND

Patient monitors have traditionally displayed vital sign data for patients. For example, a multifunction patient monitor may display vital sign data such as one or more of: electrocardiograph (ECG) trend line(s), cardiac pulse rate, a respiration rate and/or trend line, blood oxygen saturation ($SpO_2$) value and/or trend line, blood pressure value and/or trend line, capnography trend line and/or end-tidal carbon dioxide ($etCO_2$) level, and/or so forth. Such a patient monitor provides a large amount of patient data from which a doctor, nurse, or other medical professional can assess patient status.

However, a difficulty with such a patient monitor is that it requires the medical professional to possess the clinical expertise to interpret the various vital signs, and in particular to interpret the combination of vital sign data provided by the patient monitor. Even more, the interpretation may require or benefit from additional information not captured and displayed by the patient monitor, such as patient medical history and/or the patient•s most recent laboratory test results, e.g. arterial blood gas (ABG), whole blood count (WBC) data, and/or so forth. The patient•s medical status may be inaccurately assessed based on data presented by the patient monitor if the medical professional has insufficient clinical expertise, insufficient knowledge (e.g. not aware of the latest laboratory test results), and/or insufficient time to properly analyze the large quantity of information presented by the patient monitor.

Time constraints in interpreting data presented by a patient monitor can be particularly problematic during a surgery or other interventional medical procedure, where it may be desired to track the real-time risk of contracting an adverse medical condition. For example, during an image guided therapy (iGT) procedure, the administration of intravenous contrast agent so as to improve guidance image contrast may need to be balanced against the potential for kidney injury due to the contrast agent. This risk of kidney injury depends on factors such as patient medical history (e.g., a diabetic patient is at heightened risk of contrast agent-induced kidney injury) and blood pressure. Synthesizing the relevant information to assess kidney risk during the iGT procedure is a challenging task.

A known improvement in patient monitoring incorporates a risk estimation tool into the patient monitor. For example, a nomogram may be provided that graphically represents the risk of an adverse condition to the patient given certain inputs (e.g. vital signs) to the nomogram. In electronic form, the nomogram may be replaced by equivalent computer processing to compute the risk of adverse condition onset given the inputs. A risk estimation tool can succinctly present the aggregate impact of the combination of vital signs or other inputs on risk of the patient contracting the adverse condition.

The following discloses new and improved systems and methods.

SUMMARY

In one disclosed aspect, a patient monitoring device includes a display. Processing hardware includes an electronic processor and a non-transitory storage medium storing a database of visualization templates and instructions readable and executable by the electronic processor to perform a patient monitoring method including: obtaining patient values for one or more known variables of a risk prediction function; determining one or more unknown variables of the risk prediction function for which patient values are not known and defining at least one hyperplane as values that can be assumed by the one or more unknown variables; computing values of the risk prediction function over the at least one hyperplane using the obtained patient values for the one or more known variables; selecting a visualization template from the database of visualization templates using template selection indices including the risk prediction function and the one or more unknown variables; and, using the visualization template, displaying on the display a visualization of the computed values of the risk prediction function over the at least one hyperplane.

In another disclosed aspect, a patient monitoring method is disclosed. At a bedside or surgical patient monitor, patient values are obtained for one or more known variables of a risk prediction function. Using processing hardware including an electronic processor, one or more unknown variables of the risk prediction function are determined for which patient values are not known, and at least one hyperplane is defined as values that can be assumed by the one or more unknown variables. Using the processing hardware, values of the risk prediction function are computed over the at least one hyperplane using the obtained patient values for the one or more known variables. On a display of the bedside or surgical patient monitor, a visualization is displayed of the computed values of the risk prediction function over the at least one hyperplane.

In another disclosed aspect, a patient monitoring device is disclosed, including an image guided therapy (iGT) device including a radiological imaging component and a surgical display. Processing hardware includes an electronic processor and a non-transitory storage medium storing instructions readable and executable by the electronic processor to compute the value of a risk prediction function and to perform a patient monitoring method including: displaying, on the surgical display of the iGT device, images of a patient acquired using the radiological imaging component of the iGT device; obtaining patient values for one or more known variables of the risk prediction function; determining one or more unknown variables of the risk prediction function for which patient values are not known and defining at least one hyperplane as values that can be assumed by the one or more unknown variables; computing values of the risk prediction function over the at least one hyperplane using the obtained patient values for the one or more known variables; and displaying, on the surgical display of the iGT device, a visualization of the computed values of the risk prediction function over the at least one hyperplane.

One advantage resides in providing a patient monitoring device including a risk estimation tool for assessing risk of a patient contracting an adverse condition, in which the risk estimation tool accommodates missing input data.

Another advantage resides in providing such a risk estimation tool that provides information on the impact on of unknown discrete options, e.g. whether or not a therapy option is employed.

Another advantage resides in providing such a risk estimation tool that provides information on the impact on of unknown continuous options, e.g. providing guidance on the extent to which a quantitative dosage of a pharmaceutical impacts the risk.

Another advantage resides in providing a compact graphical representation of the risk of a patient contracting an adverse condition.

Another advantage resides in providing such a compact graphical representation of the risk which also depicts the impact of missing input data.

Another advantage resides in providing a risk estimation tool for estimating risk of the patient contracting acute kidney injury (AKI) during an image-guided therapy (iGT) procedure, in which the AKI risk estimation tool has one or more of the foregoing benefits.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

As recognized herein, a difficulty with risk estimation tools is that the tool employs a risk prediction function that requires certain inputs. For example, an acute kidney injury (AKI) risk estimation tool for estimating risk of contracting AKI during a surgical procedure may require the following input variables: hypotension; periprocedural use of an intra-aortic balloon pump (iABP); chronic heart failure; age; anemia; diabetes; contrast medium volume; and estimated glomerular filtration rate (eGFR, a metric of kidney function). Of these variables, hypotension, iABP, chronic heart failure, anemia, and diabetes are binary variables representing whether the patient has these conditions (or whether the iABP is used). The age, contrast medium volume, and eGFR variables each assume a numerical value. Based on the status of these input parameters the AKI model produces a percentage risk score or risk score category (low/medium/high) that can be displayed to the operator for intervention planning and/or consideration during the performance of the interventional procedure. Similar risk estimation techniques have been developed for other adverse events, such as medication and radiation overdose. Risk models are a type of prediction tool designed to predict a certain event based on input health variables. Prediction tools can be used before and/or during a medical procedure. They can also be used to weigh the risk/benefit of a contemplated medical procedure or treatment option.

Generally, input variables of a prediction tool can be categorized as static or dynamic. A static variable is known and is not expected to change substantially within a timeframe that is realistic for the prediction tool•s use and intent. Examples include diabetes and age. A dynamic variable will become known, and/or will change substantially, within a timeframe that is realistic for the prediction tool•s use and intent. Examples include contrast medium volume. In the context of a medical procedure (e.g., the AKI risk estimation tool applied to estimate likelihood of contracting AKI during a coronary intervention), the realistic timeframe suitably includes the planning phase leading to the procedure as well as the duration of the procedure itself. In this context, a third category of input variable can be distinguished, namely an unknown variable. This variable remains unknown before and during the relevant timeframe.

If a prediction tool entirely depends on static variables, those can be obtained before the medical procedure and used to derive the predicted risk. However, many risk estimation tools rely on variables that are dynamic and/or unknown. In such cases, the risk estimation tool either cannot be used, or can only be used by making •best guess, estimates for the values for the unknown variable(s). Such estimates in some instances do not have a rational basis, and/or have a high likelihood of being significantly in error. Medical decisions made on the basis of risk estimated using such a risk estimation tool are also suspect, and could lead to non-optimal decisions. Furthermore, even if the •best guess, estimate for an unknown input variable is a reasonable estimate, this approach provides a single (estimated) data point for the predicted risk of the adverse event. If the unknown variable is controllable by medical personnel, then it would be useful for the risk prediction tool to provide information as to the impact of choosing different values for the unknown (but controllable) variable.

In embodiments disclosed herein, a risk prediction tool operates by obtaining patient values for one or more known variables of a risk prediction function. In this data gathering process, one or more unknown variables of the risk prediction function are determined, for which patient values are not known. At least one hyperplane is defined as values that can be assumed by the one or more unknown variables, and values of the risk prediction function are computed over the at least one hyperplane using the obtained patient values for the one or more known variables. A visualization template is selected from a database of visualization templates using template selection indices including the risk prediction function and the one or more unknown variables. The computed values of the risk prediction function over the at least one hyperplane are displayed using the visualization template.

This approach for an improved risk prediction tool is premised on various insights made herein. First, while the space defined by all input variables of a risk prediction function is usually very large, the set of possible unknown variables is quite small. Using the AKI risk prediction tool previously mentioned, there are eight input variables: hypotension, iABP, chronic heart failure, age, anemia, diabetes, contrast medium volume, and eGFR. The possible values that may be assumed by these eight variables is large: the five binary variables (hypotension, iABP, chronic heart failure, anemia, and diabetes) have $2^5=32$ combinations, and for each of these 32 combinations, the remaining three numeric variables (age, contrast medium volume, and eGFR) can assume any of dozens, hundreds or more values, depending upon the granularity or resolution used for these values.

On the other hand, the total number of unknown variables can be no more than eight, and in realistic situations is likely to be no more than two or three. In the AKI risk prediction tool example, it is likely that hypotension, chronic heart failure, age, anemia, and diabetes will have known values, e.g. retrieved from an electronic patient or health record. Thus, the total number of unknown variables is likely to be at most three: iABP, contrast medium volume, and eGFR. If one or two of these variables is known a priori (for example, the surgeon may make a pre-procedural decision that this patient must have an iABP due to cardiac disease, and/or may decide prior to the procedure that a certain contrast medium volume is to be used), then the number of unknown variables is suitably reduced.

For three unknown variables as per the previous example, two hyperplanes are defined: one hyperplane for iABP=•false, and another hyperplane for iABP=•true. Each hyperplane is defined as the set of values that can be assumed by the remaining two unknown variables (contrast medium volume and eGFR). It is computationally feasible to compute the values of the AKI risk prediction function over these two hyperplanes using the obtained patient values for the one or more known variables (and the appropriate iABP value for each hyperplane). The visualization is also feasible, since there is a small space of possible visualizations that may need to be presented which can have corresponding visualization templates: one template for all three variables unknown; three templates for the three possible combinations of two unknown variables, and three possible combinations of one unknown variable (seven templates in all). If one or two the other binary variables may also be realistically unknown (e.g. hypotension) then this merely increases the number of templates by a factor of two.

Thus, it is computationally feasible to compute and display a visualization designed for the particular risk prediction function and the specific set of unknown variables encountered in a specific patient situation. This is done by providing the (limited) set of visualization templates each indexed by selection indices including the risk prediction function and the unknown variables. Optionally, the visualization templates may be indexed by other information: for example, there may different visualization templates provided using different formats, e.g. one tailored for use during a surgical procedure and another tailored for general patient monitoring in a critical care unit.

Figure 1:
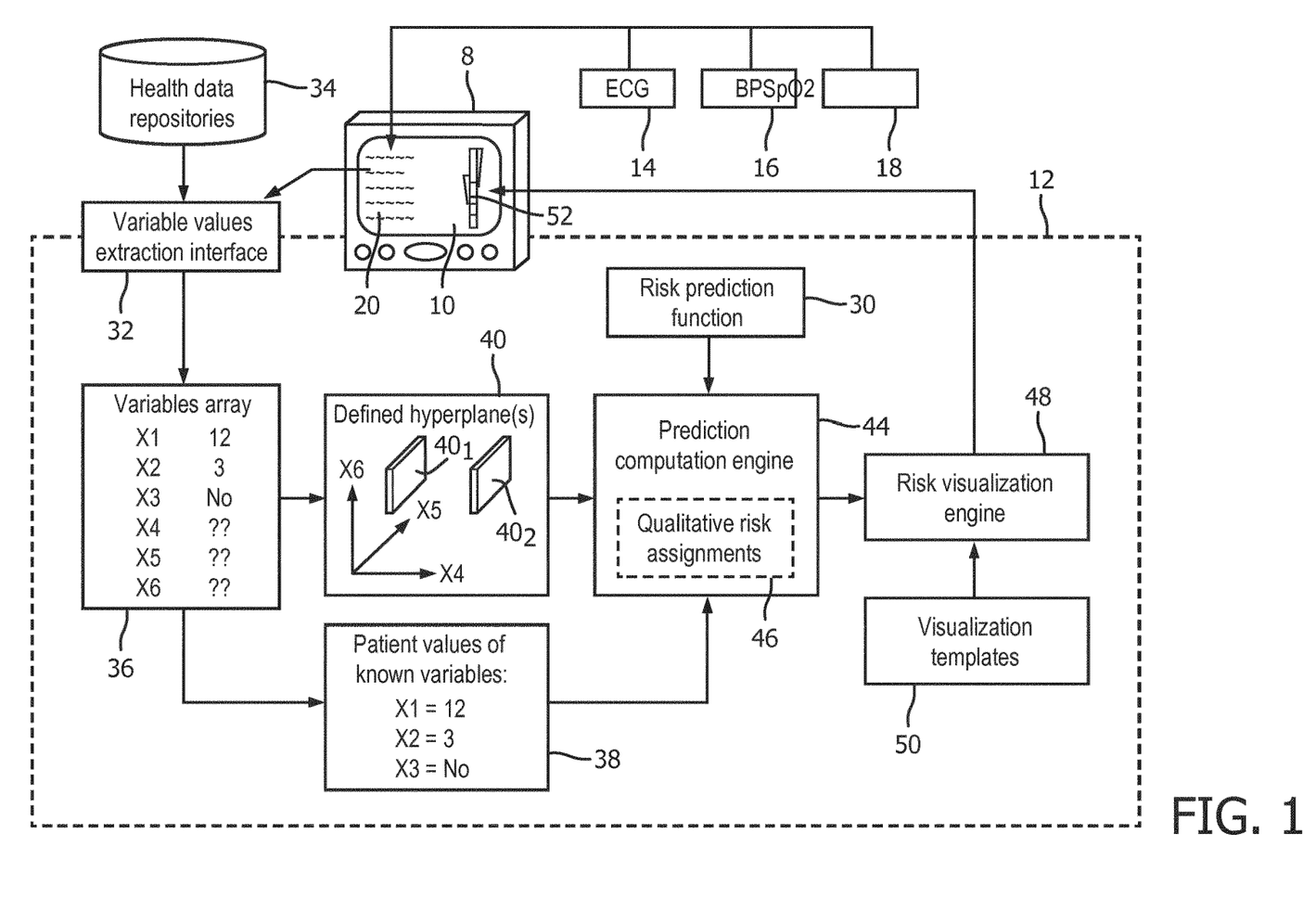
FIG. 1 diagrammatically illustrates a patient monitoring device including a patient monitor having a risk estimation tool.

With reference to FIG. 1, in an illustrative example, a risk prediction tool is part of a patient monitor, and is incorporated into a bedside or surgical patient monitor 8 including a display 10. The patient monitor further includes processing hardware 12 including an electronic processor and a non-transitory storage medium. The electronic processor may, by way of non-limiting illustrative example, comprise a microprocessor or microcontroller of the bedside or surgical patient monitor 8 and ancillary electronics such as memory, graphical processing unit and/or so forth; and/or may comprise a remote server computer with which the bedside or surgical patient monitor 8 is operatively connected via a hospital electronic network and/or the Internet; and/or may comprise a computer or other processing electronics of an image-guided therapy (iGT) device; and/or so forth. The non-transitory storage medium may likewise be internal to the bedside or surgical patient monitor 8 and/or may reside at or in an operatively connected server computer, iGT device, or so forth. The non-transitory storage medium may comprise a hard disk drive, RAID, or other magnetic storage medium; an optical disk or other optical storage medium; a solid state drive or other electronic storage medium; various combinations thereof; and/or so forth. The processing hardware 12 is diagrammatically indicated in FIG. 1; it is to be understood that the processing hardware 12 is implemented as instructions stored on the non-transitory storage medium that are readable and executable by the electronic processor to perform operations as disclosed herein. The non-transitory storage medium also stores various data structures (e.g. data arrays, visualization templates, or so forth) accessed and used in the disclosed operations.

The illustrative bedside or surgical patient monitor 8 is operatively connected to receive vital sign data from one or more vital sign sensors, e.g. an illustrative electrocardiogram (ECG) or other cardiac monitor 14, a blood pressure sensor 16 (e.g. a blood pressure cuff, an arterial line blood pressure monitor, and/or so forth), a pulse oximeter 18 measuring oxygen saturation ($SpO_2$) and optionally also heart rate, and/or so forth. In practical use, the vital sign sensors 14, 16, 18 are connected to a patient whose medical condition is being monitored by the bedside or surgical patient monitor 8, and the operative connection with the monitor 8 may be by a wired connection or a wireless connection (e.g. Bluetooth f, WiFi, et cetera). The received vital sign data (or some sub-set thereof) may optionally be displayed in a suitable window or display area 20. The processing hardware 12 may also be programmed to perform various data processing on the vital sign data, e.g. extracting heart rate, ST elevation, or other information from ECG traces; extracting systolic and diastolic pressure readings from blood pressure data; and/or so forth.

The processing hardware 12 is also programmed to implement a risk prediction tool applied to assess risk of the patient contracting an adverse medical condition. To this end, the processing hardware 12 obtains patient values for one or more known variables of a risk prediction function 30, and also determines one or more unknown variables of the risk prediction function for which patient values are not known. A variable values extraction interface 32 is implemented by the processing hardware 12, and possibly by other associated hardware such as an electronic hospital network and/or the Internet providing operative access to one or more health data repositories 34 such as an Electronic Medical Record (EMR), Electronic Health Record (EHR), Cardiovascular Information System (CVIS), Radiology Information System (RIS), and/or so forth. An application programming interface (API) may be employed to query for patient-specific documents using a patient identifier (e.g., a medical record number). The variable values extraction interface 32 may also receive one or more values of input variables for the risk prediction function 30 from one or more of the vital sign sensors 14, 16, 18 (again, possibly with some post-acquisition processing of the vital sign data performed by the processing hardware 12). It is also contemplated for the variable values extraction interface 32 to provide a user dialog in conjunction with the display 10 and a keyboard, mouse, dictation microphone, or other user input device, via which a user may enter the value(s) of one or more input variables. It may be noted that an input variable can be composed of elementary variables itself. For instance, the eGFR parameter of the illustrative AKI model is determined using a mathematical formula applied to the following elementary variables: serum creatinine; age; gender; and race. In such cases, the variable may be computed from the underlying elementary variables received via the repository 34, vital sign sensors 14, 16, 18, or manual input. A variables array 36 stores the values of all input variables which are known, with any unknown variables assigned placeholder indicators (denoted as question marks in FIG. 1) or otherwise indicated to be determined to be unknown variables.

The set of input variables are then divided into two groups: the first group is the known variables, for which patient values 38 are known. The second group is the unknown variables, for which patient values are not known. The processing hardware 12 is programmed to define at least one hyperplane 40 as values that can be assumed by the one or more unknown variables. For example, in diagrammatic FIG. 1 there are three unknown variables: X4, X5, and X6. Of these, X4 is a binary value. Setting X4 to one value it can assume (e.g. "false" or "no" or so forth depending upon the information represented), a first hyperplane 40$_1$ is defined by the values that can be assumed by the (X5, X6). Likewise, setting X4 to the other value it can assume (e.g. "true" or "yes" or so forth), a second hyperplane 40$_2$ is defined by the values that can be assumed by the (X5, X6). In this example, the hyperplanes 40$_1$, 40$_2$ are each two dimensional "true" planes; on the other hand, if there were three or more continuous variables the hyperplanes would be higher-dimensional; conversely, if there were only a single continuous variable the hyperplane would be one-dimensional, i.e. a line. As used herein, the term "hyperplane" encompasses all these cases (one-dimensional, two-dimensional, three-dimensional, or higher-dimensional). The range of the hyperplane(s) is controlled by the values that the various unknown variable(s) can credibly assume. For example, if one of the unknown variables is heart rate, then the credible range for this variable may be, e.g. 40-200 beats per minute (bpm). The credible range for SpO$_2$ may be 0-100% or, more realistically, some higher lower limit such as 50-100%. As previously implied, the credible range for X4 is the set {"false", "true"} or {"no", "yes"} or so forth depending upon the represented information. In the case of continuous variables, the hyperplane(s) 40 may be discretized for more convenient computation: for example, the hyperplane may be defined by data points for discrete heart rates in increments of 5 bpm (e.g. 40 bpm, 45, bpm, 50 bpm, . . . , 200 bpm), with the resolution chosen to balance the smoothness of the eventual visualization against computational efficiency and speed.

The processing hardware 12 is programmed to implement a prediction computation engine 44 which computes values of the risk prediction function 30 over the at least one hyperplane 40 using the obtained patient values 38 for the one or more known variables. This entails looping through the credible values of the unknown variables spanning the hyperplanes. For example, using the unknowns X4, X5, X6 of the diagrammatic example of FIG. 1 with X5 being heart rate in the range 40-200 bpm and X6 being SpO$_2$ in the range 50-100%, this entails invoking the risk prediction function 30 to compute the risk for the set of inputs:

(X1=12, X2=3, X3=•No, X4=•false X5=40, X6=50%)
(X1=12, X2=3, X3=•No X4=•false X5=40, X6=55%)
(X1=12, X2=3, X3=•No, X4=•false X5=40, X6=60%)
, , ,
(X1=12, X2=3, X3=•No, X4=•false X5=40, X6=100%)
(X1=12, X2=3, X3=•No, X4=•false X5=45, X6=50%)
(X1=12, X2=3, X3=•No, X4=•false X5=45, X6=55%)
(X1=12, X2=3, X3=•No X4=•false X5=45, X6=60%)
, , ,
(X1=12, X2=3, X3=•No, X4=•false X5=45, X6=100%)
, , ,
(X1=12, X2=3, X3=•No, X4=•false X5=200, X6=100%)
(X1=12, X2=3, X3=•No X4=true X5=40, X6=50%)
, , ,
(X1=12, X2=3, X3=•No X4=true X5=200, X6=100%)

Optionally, the values of the risk prediction function 30 computed by the prediction computation engine 44 are discretized into qualitative risk assignments 46, e.g. if the risk prediction function 30 is an AKI risk prediction function then the values of the AKI risk prediction function may be binned into qualitative risk assignments labeled •low, •medium, •high, and •very high. More generally, the qualitative risk assignments 46 map the prediction value (or score) onto a qualitative state. In one implementation, it has a range associated with each qualitative state. This range may be locally configurable to reflect local practices. In another implementation, each qualitative state may itself be marked. For instance, we can distinguish: (1) hard bound states: the qualitative state requires termination of the medical procedure or otherwise inappropriate state of affairs; versus (2) soft bound states: the qualitative state is of concern, but if no other options are available, the medical procedure may continue. In addition, the qualitative risk assignments 46 may be capable of computing borderline combinations of unknown input parameters for each qualitative state. For instance, in the example of the AKI model, assume that contrast medium volume is the only unknown (i.e., all other input parameters are in the variables array 36). Then, the minimum and maximum amounts of contrast medium volume can be computed that will yield a •medium, risk qualitative state by means of the Prediction score computation engine 44. In one implementation, it does it by iterating through all relevant combinations of unknown input parameters. This method can also be used for two or more missing unknown parameters by iterating through all pairs of unknown input parameters. This method can be applied for select qualitative states (e.g., only hard bound).

The processing hardware 12 is programmed to implement a risk visualization engine 48 that selects a visualization template from a database of visualization templates 50 using template selection indices including the risk prediction function 30 to be visualized and the one or more unknown variables (namely variables X4, X5, and X6 in the diagrammatic example of FIG. 1), and displays (on the display 10) the computed values of the risk prediction function 30 over the at least one hyperplane 40 as a visualization 52 using the selected visualization template. The visualization template defines the graphical representation and how the values of the risk prediction function are displayed in that graphical representation. An illustrative example is described elsewhere herein with reference to FIG. 3.

Figure 2:
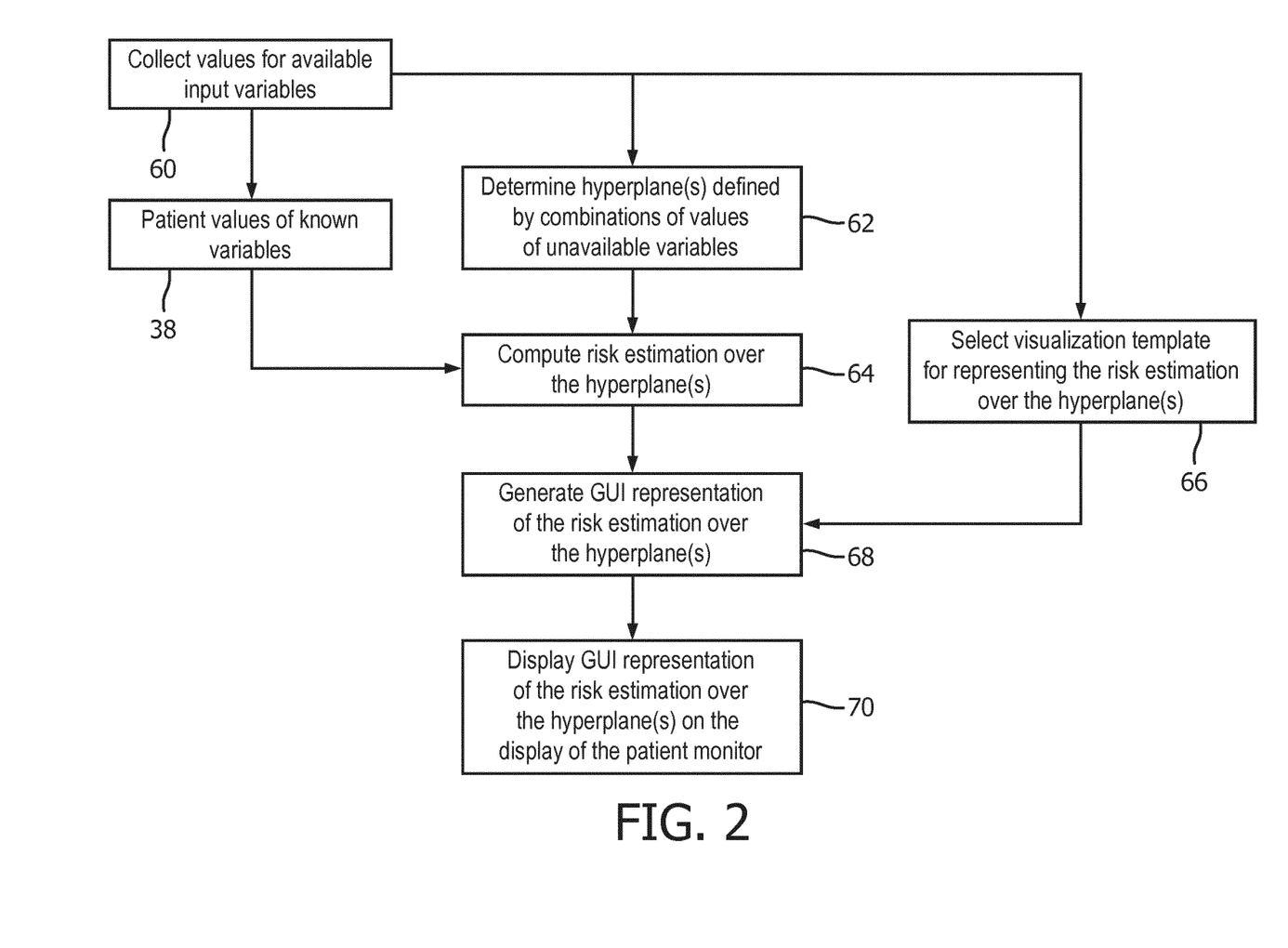
FIG. 2 diagrammatically illustrates a risk estimation process performed by the patient monitoring device of FIG. 1.

With continuing reference to FIG. 1 and with further reference to FIG. 2, a risk estimation process performed by the patient monitor of FIG. 1 is described. In an operation 60 the extraction interface 32 is used for obtaining patient values 38 for one or more known variables of a risk prediction function. The operation 60 also determines one or more unknown variables of the risk prediction function for which patient values are not known, and an operation 62 determines the hyperplane(s) 40 defined by combinations of credible values of the unknown variables. In an operation 64, the prediction computation engine 44 computes values of the risk prediction function 30 over the at least one hyperplane 40 using the obtained patient values 38 for the one or more known variables. In an operation 66, the visualization template for visualizing the computed values is selected from the visualization templates database 50 using indices including the risk prediction function 30 and the unknown variables. In an operation 68, the risk visualization engine 40 generates a graphical user interface (GUI) representation (i.e. visualization) of the risk estimation over the hyperplane(s) 40 using the selected visualization template. In an operation 70 the risk visualization engine 40 displays the GUI representation (i.e. visualization) on the display 10.

It should be noted that the risk estimation is preferably dynamic. If a patient value is received for a previously unknown variable, then the method of FIG. 2 can be re-executed to update the visualization. Likewise, if the patient value of a known variable changes, as can be the case for a dynamic variable such as a vital sign that may change over time, the method of FIG. 2 can be re-executed to update the visualization.

Figure 3:
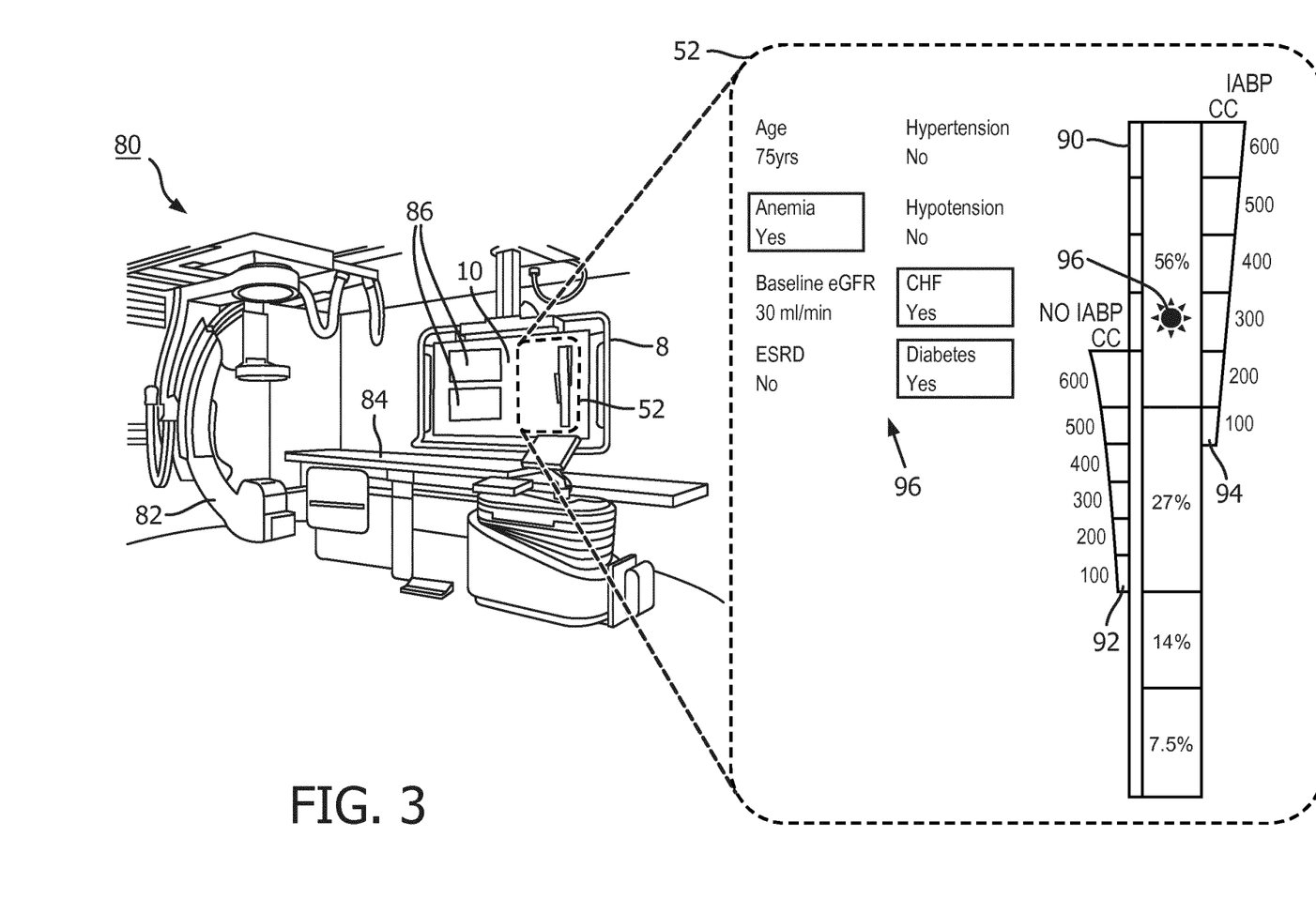
FIG. 3 diagrammatically illustrates a patient monitoring device including an x-ray based image guided therapy (iGT) device with a surgical display providing a graphical user interface (GUI) risk estimate presentation generated by the process of FIG. 2, which represents risk of a patient contracting acute kidney injury (AKI) during an interventional procedure performed while the patient is monitored by the x-ray based iGT device.

With reference to FIG. 3, in some embodiments the patient monitor 8 may be part of an image guided therapy (iGT) device 80, and may be used to provide a risk prediction for an adverse condition that is updated in (near) real time over the course of the interventional procedure. In an illustrative example, the risk that is predicted is the risk of acute kidney injury (AKI). This risk is heightened under certain circumstances, such as the use of an intra-aortic balloon pump (iABP), and the use of certain contrast agents, e.g. iodinated contrast medium of the type sometimes used to increase vascular contrast when using a transmission x-ray imaging device such as a computed tomography (CT) imaging device during a cardiac or vascular surgical procedure. The illustrative iGT device 80 employs a C-arm type x-ray imaging component 82, which permits tomographic or multi-view cardiac imaging of a patient (not shown) disposed on an examination table 84. An illustrative example of such an iGT device is the Azurion 7 series iGT devices, available from Koninklijke Philips N.V. (Eindhoven, the Netherlands). In this embodiment, the surgeon can view images 86 acquired by the radiological imaging component 82 on the display 10, along with the visualization 52 generated by the risk prediction tool.

With continuing reference to FIG. 3, an enlarged view of an illustrative visualization 52 suitably output by an AKI risk prediction tool is shown. This illustrative visualization displays two unknown parameters: one discrete (use of iABP during procedure, that is, the binary iABP variable) and one numeric (the contrast medium variable indicating contrast agent volume with an illustrative range [0, 600 cc]). In the illustrative visualization 52, a vertical bar 90 representing AKI risk is partitioned in twenty segments, each corresponding to a prediction score of the AKI risk prediction function. The twenty segments are further grouped (i.e. discretized) into four non-overlapping groups labeled •7.5%, •14%, •27% and •56%, to mark four qualitative AKI risk states. The •7.5%, group represents low risk: segments 1 to 5. The •14%, group represents medium risk: segments 6 to 10. The •27%, group represents high risk: segments 11 to 15. The •56%, group represents very high risk: segments 16 to 20. In the illustrative AKI risk visualization, the two possible values that may be assumed by the iABP variable are captured by: a first risk plot 92 showing the AKI risk as a function of contrast agent volume in the case where no iABP is used; and a second risk plot 94 showing the AKI risk as a function of contrast agent volume in the case where iABP is used. A numerical table portion 96 shows the patient values of the known variables which are also inputs to the AKI risk prediction function 30.

Advantageously, the illustrative AKI risk visualization 52 shown in FIG. 3 provides the surgeon with a substantial amount of information available at a glance. For example, if the surgeon is contemplating deploying an iABP during the cardiac procedure, the surgeon can compare the risk plots 92, 94 to rapidly assess the increase in AKI risk that would be engendered by deploying an iABP. The surgeon may also understand, again at a glance, that the use of an iABP could be compensated by reducing the contrast agent volume, e.g. the AKI risk without an iABP at 500 cc contrast agent is comparable with the risk with an iABP at a lower dose of 150 cc contrast agent.

Conventionally, where input variables for a risk function are unknown, these values are assigned default values and a risk is computed. Optionally, to provide the surgeon with this same information in the context of the visualization 52, a default value of the risk prediction function may be computed using the obtained patient values 38 for the one or more known variables and default values for the one or more unknown variables (here iABP and contrast agent volume), and a marker 96 may be employed to mark the default value of the risk prediction function 30 on the display of the computed values of the risk prediction function over the at least one hyperplane (i.e. on the visualization 52).

In the following, some further illustrative examples are described. Table 1 provides a summary of the terminology and notation employed in these examples, with some further explanation of certain terms and notation given in the text below.

In the following examples, the risk prediction function 30 is represented as risk prediction function F that has n input variables (also referred to herein as parameters): $x_1, \ldots, x_n$. The output of the function is denoted by $F(x_1, \ldots, x_n)$. The output may be numeric or discrete (e.g., an integer in [0, 20]). The risk prediction function 30 may be implemented computationally by machine learning classification models, neural networks, Random Forests and Support Vector Machines (SVMs), logistic and linear regression models, various combinations thereof, so forth.

As an illustrative example, consider a risk prediction function F with two input variables x and y. If x is static (that is, a known variable), e.g., x=12, and y is an unknown variable, then the •residual function, $F_{12}$ has one input parameter, such that $F_{12}(y)=F(12, y)$. Such residual functions can be derived for any function and any number of static variables it may have.

If the output of risk prediction function F is a value from a list, it is likely that the values have a readily apparent meaning, but this may not always be the case. An optional •qualitative state, may be provided, which is the interpretation of the output of a (residual) function. For instance, the illustrative AKI model may return 11 risk points as the predicted risk for acute kidney injury. The corresponding qualitative state may be •Medium risk.

TABLE 1

| | Description | Source |
|---|---|---|
| Variable (or Parameter) | Input to a function (e.g., diabetic status of the patient) | Extracted by extraction interface 32; optionally reviewed by human |
| Risk prediction function | A mathematical object that underlies a prediction tool converting one or more variables into a prediction score | Obtained from literature and/or clinical knowledge/expertise |
| Residual function | Derived from the risk prediction function by fixing at least one but not all variables of the risk prediction function. A residual function is itself a mathematical function. | Residual functions can be derived, or generated by taking the risk prediction function and the patient values 38 of the known variables of the variables array 36 |
| Prediction score | Output of the risk prediction Function or of a residual function derived from the risk prediction function | Computed by prediction computation engine 44 |
| Qualitative state | A controlled information item onto which predication scores are mapped. | The mapping is executed by the qualitative risk assignments 46. A set of qualitative states may reflects a local (e.g. hospital) preference and may optionally be a configurable aspect of the prediction computation engine 44. For instance, in one hospital the AKI risk prediction score •18, may be mapped onto the qualitative state •Unacceptable . . . procedure terminated, in one care setting, whereas it is mapped onto •Very high risk, in another. |

Some further examples of the hyperplane(s) 40 are as follows. As an initial point, if all parameters are known, then no hyperplane is defined and the prediction computation engine 44 simply inputs the known variables to the risk prediction function 30 to receive a prediction score. If one or more parameters are unknown, it defines a hyperplane depending on the nature of the unknown parameters. By means of example, consider the following cases.

In one class of hyperplanes, only one parameter is unknown, and it is numeric (e.g. contrast medium volume with range [0, 600]). Then, the hyperplane is a line with x coordinates in the range [0, 600] and y coordinates determined by applying the risk prediction function 30 based on the variables array 36 and the x coordinates with increments along x chosen to be small enough for desired resolution and large enough to provide acceptable computational efficiency.

In another class of hyperplanes, only one parameter is unknown and it is discrete, e.g. the iABP variable which can assume values of the set {yes, no}. Then, the hyperplane is reduced to two prediction scores: the one obtained by evaluating the risk prediction function 30 with all other known parameters and with the unknown iABP variable set to •yes, and the other obtained similarly with the unknown iABP variable set to •no.

In another class of hyperplanes, two parameters are unknown, one is numeric (e.g. contrast agent volume with range [0, 600]), one is discrete, e.g. the iABP variable which can assume values of the set {yes, no}. In this case, the hyperplane consists of two lines: one obtained by fixing the unknown iABP variable to •yes, and iterating over the numeric unknown contrast agent volume variable for small increments in the range; and the other obtained by fixing the unknown iABP variable to •no, and iterating over the numeric unknown contrast agent volume variable for small increments in the range.

In another class of hyperplanes, two parameters are unknown, both of which are numeric. Then, the defined hyperplane is a plane in three-dimensional space, with x and y coordinates in the ranges of the two unknown parameters and z coordinate determined by feeding the two coordinates to the risk prediction function 30 in addition to the remaining parameters all of which are known.

The foregoing are illustrative examples, and can be generalized to the general case of an arbitrary number of unknown variables.

In embodiments including the qualitative risk assignments 46, (fragments of) the hyperplane can be tagged with qualitative states. This can be achieved by looping through each input parameter vector $(x_1, , , , , x_n)$ obtaining the prediction score from the hyperplane that was computed using the risk prediction function 30 and mapping this prediction score onto a qualitative state. Thus each input parameter vector $(x_1, , , , , x_n)$ can be tagged with a qualitative state. Optionally, minimum and maximum input variable vectors are also derived for each qualitative state with regards to the known variables. In this manner, for instance, a minimum and maximum contrast agent volume dose can be computed for a qualitative state denoted as •Unacceptable . . . terminate procedure.

As previously mentioned, the prediction computation engine 44 can be triggered whenever the variables array 36 is updated with a change in a patient value for one of the variables, so that is responds to changes in patient values of the input variables in real time. Alternatively, the prediction computation engine 44 can be triggered periodically or when the user interacts with it.

The risk visualization engine 48 presents the values of the risk prediction function 30 computed over the hyperplane(s) by the prediction computation engine 44. Various visualization graphics may be employed. For example, if the hyperplane is one or more scores, it may display these, for instance as a bar plot. If the hyperplane is a line, it may display the line, for instance, as a trend line diagram. If the hyperplane is a plane in three-dimensional space, it may display it as a three dimensional plot. The current, or default, position 96 (see FIG. 3) can be marked in the display. This default position can be computed by using default parameters values for the unknown variable(s). In another contemplated variant embodiment, a delta can be displayed from the presumed current or default position, marking what is the difference in prediction score if the value of any one unknown variable changes with a preset increment. In this manner, for instance, the additional risk for AKI can be computed for using 100 cc of contrast medium volume. In another contemplated embodiment, The risk visualization engine 48 is interactive and allows manual entry of one unknown variable by touching a position on any of the respective axis corresponding to an unknown parameter (e.g., mark contrast volume=200 cc by touching either the first risk plot 92 shown in FIG. 3 if no iABP is used, or the second risk plot 92 if iABP is used). In addition, touch screen interaction can serve to determine a coordinate in the display that is marked as •current, updating the delta if that information was shown. If the qualitative risk assignments 46 is implemented, the qualitative states can be visualized by color-coding the areas in the hyperplane with matching qualitative states (e.g., in FIG. 3, the segments labeled •7.5%, •14%, •27%, and •56%, can each have a different color, for example running from blue to red to indicate increasing AKI risk). If the qualitative risk assignments 46 provides bounds on qualitative states, those bounds can be marked explicitly, e.g., by a thick line.

By virtue of the database of visualization templates 50, custom visualizations can be implemented to display the hyperplane information in a manner that is geared to a particular clinical situation or medical domain. An illustrative example has been described with reference to FIG. 3 as the AKI risk visualization 52 designed for an iGT device 80.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

What is claimed is:

1. A patient monitoring device comprising:
   a display;
   processing hardware including an electronic processor and a non-transitory storage medium storing a database of visualization templates and instructions readable and executable by the electronic processor to perform a patient monitoring method including:
   obtaining patient values for one or more known variables of a risk prediction function;
   defining at least one hyperplane as values that can be assumed by one or more unknown variables of the risk prediction function for which patient values are not known;
   computing values of the risk prediction function over the at least one hyperplane using the obtained patient values for the one or more known variables to determine the values of the risk prediction function;
   selecting a visualization template from the database of visualization templates using template selection indices including the risk prediction function and the one or more unknown variables;
   using the visualization template, displaying on the display a visualization of the computed values of the risk prediction function over the at least one hyperplane; and
   based on the visualization, administer at least one of a contrast agent and an intra-aortic balloon pump to a patient.

2. The patient monitoring device of claim 1 wherein the patient monitoring method further includes receiving vital sign data from one or more vital sign sensors, wherein the obtaining includes obtaining at least one patient value as vital sign data received by the electronic processor from the one or more vital sign sensors.

3. The patient monitoring device of claim 2 wherein the patient monitoring method further includes displaying received vital sign data on the display separately from the display of the computed values of the risk prediction function.

4. The patient monitoring device of claim 1 wherein the patient monitoring method further includes:
   computing a default value of the risk prediction function using the obtained patient values for the one or more known variables and default values for the one or more unknown variables; and
   displaying a marker indicating the default value of the risk prediction function on the visualization.

5. The patient monitoring device of claim 1 further comprising:
   an image guided therapy (iGT) device including a radiological imaging component;
   wherein the risk prediction function comprises an acute kidney injury (AKI) risk prediction function and the variables of the AKI risk prediction function include a contrast agent dose variable representing a dose of contrast agent administered to the patient to improve image contrast of an image acquired of at least a portion of the patient by the iGT device.

6. The patient monitoring device of claim 1 wherein the risk prediction function comprises an acute kidney injury (AKI) risk prediction function and the variables of the AKI risk prediction function include an intra-aortic balloon pump (iABP) variable indicating whether an iABP is employed during a surgical procedure performed on the patient while performing the patient monitoring method.

7. A patient monitoring method comprising:
   at a bedside or surgical patient monitor, obtaining patient values for one or more known variables of a risk prediction function;
   with an image guided therapy (iGT) device, acquiring one or more images of a patient;
   using processing hardware including an electronic processor, determining one or more unknown variables of the risk prediction function for which patient values are not known and defining at least one hyperplane as values that can be assumed by the one or more unknown variables of the risk prediction function for which patient values are not known;
   using the processing hardware, computing values of the risk prediction function over the at least one hyperplane using the obtained patient values for the one or more known variables to determine the values of the risk prediction function;
   on a display of the iGT device, displaying the acquired images and a visualization of the computed values of the risk prediction function over the at least one hyperplane; and
   based on the visualization, administer a contrast agent to a patient.

8. The patient monitoring method of claim 7 further comprising:
   generating the visualization by populating a visualization template with the computed values of the risk prediction function over the at least one hyperplane.

9. The patient monitoring method of claim 8 further comprising:
   selecting the visualization template from a database of visualization templates using template selection indices including the risk prediction function and the one or more unknown variables.

10. The patient monitoring method of claim 7 wherein the determining includes determining a discrete unknown variable and at least one continuous unknown variable and defining the at least one hyperplane as a hyperplane for each discrete value that the discrete unknown variable can assume wherein each hyperplane is further defined by the values that can be assumed by the at least one continuous unknown variable.

11. The patient monitoring method of claim 7 further comprising:
   receiving vital sign data from one or more vital sign sensors at the bedside or surgical patient monitor;
   wherein the obtaining includes obtaining at least one patient value as vital sign data received at the bedside or surgical patient monitor from the one or more vital sign sensors.

12. The patient monitoring method of claim 11 further comprising:
   displaying received vital sign data on the display of the bedside or surgical patient monitor separately from the visualization of the computed values of the risk prediction function over the at least one hyperplane.

13. The patient monitoring method of claim 7 wherein the obtaining includes obtaining at least one patient value from an electronic health data repository.

14. The patient monitoring method of claim 7 further comprising:
   computing a default value of the risk prediction function using the obtained patient values for the one or more known variables and default values for the one or more unknown variables; and
   displaying a marker indicating the default value of the risk prediction function on the displayed visualization.

15. The patient monitoring method of claim 7 further comprising:
   updating the obtaining, determining, computing, and displaying such that the visualization represents the current patient values for current one or more known variables of the risk prediction function.

16. The patient monitoring method of claim 7 further comprising:
   imaging the patient using an image guided therapy (iGT) device;
   wherein the one or more unknown variables include a contrast agent dose variable representing a dose of contrast agent administered to the patient to improve image contrast of an imaging performed using the iGT device.

17. The patient monitoring method of claim 16 wherein the risk prediction function comprises an acute kidney injury (AKI) risk prediction function whose value increases with increasing dose of contrast agent as represented by the contrast agent dose variable.

18. The patient monitoring method of claim 16 wherein the risk prediction function comprises an acute kidney injury (AKI) risk prediction function and the variables of the AKI risk prediction function include an intra-aortic balloon pump (iABP) variable indicating whether an iABP is employed during a surgical procedure performed on the patient while performing the patient monitoring method.

19. A patient monitoring device comprising:
   an image guided therapy (iGT) device including a radiological imaging component and a surgical display; and
   processing hardware including an electronic processor and a non-transitory storage medium storing instructions readable and executable by the electronic processor to compute the value of a risk prediction function and to perform a patient monitoring method including:
   displaying, on the surgical display of the iGT device, images of a patient acquired using the radiological imaging component of the iGT device;
   obtaining patient values for one or more known variables of the risk prediction function;
   determining one or more unknown variables of the risk prediction function for which patient values are not known and defining at least one hyperplane as values that can be assumed by the one or more unknown variables of the risk prediction function for which patient values are not known;
   computing values of the risk prediction function over the at least one hyperplane using the obtained patient values for the one or more known variables to determine the values of the risk prediction function;
   displaying, on the surgical display of the iGT device, images acquired by the iGT device and a visualization of the computed values of the risk prediction function over the at least one hyperplane; and
   based on the visualization, administer an intra-aortic balloon pump to a patient.

20. The patient monitoring device of claim 19 wherein the risk prediction function is an acute kidney injury (AKI) risk prediction function having variables including at least a contrast agent dose variable representing a dose of contrast agent administered to improve image contrast of imaging performed using the iGT device.

21. The patient monitoring device of claim 20 wherein the AKI risk prediction function has variables further including an intra-aortic balloon pump (iABP) variable indicating whether an iABP is employed during a surgical procedure performed on the patient while performing the patient monitoring method.

* * * * *